(12) United States Patent
Garzon et al.

(10) Patent No.: US 8,541,605 B2
(45) Date of Patent: Sep. 24, 2013

(54) LIPID CONJUGATED CYCLIC CARBONATE DERIVATIVES, THEIR SYNTHESIS, AND USES

(75) Inventors: Aaron Garzon, Jerusalem (IL); Jean Hildesheim, Mazkeret Batya (IL)

(73) Assignees: Siolab Ltd., Jerusalem (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 100 days.

(21) Appl. No.: 12/599,407

(22) PCT Filed: May 11, 2008

(86) PCT No.: PCT/IL2008/000651
§ 371 (c)(1),
(2), (4) Date: Jul. 7, 2010

(87) PCT Pub. No.: WO2008/139467
PCT Pub. Date: Nov. 20, 2008

(65) Prior Publication Data
US 2010/0305333 A1    Dec. 2, 2010

Related U.S. Application Data

(60) Provisional application No. 60/916,891, filed on May 9, 2007.

(51) Int. Cl.
*C07D 319/06* (2006.01)
*C07D 327/06* (2006.01)

(52) U.S. Cl.
USPC .......................................... 549/228; 549/14

(58) Field of Classification Search
USPC .................................................. 549/228, 14
See application file for complete search history.

(56) References Cited

U.S. PATENT DOCUMENTS

| | | | |
|---|---|---|---|
| 2,773,070 | A | 12/1956 | Lichtenwalter et al. |
| 2,873,282 | A | 2/1959 | McClellan |
| 5,482,965 | A | 1/1996 | Rajadhyaksha |
| 6,838,530 | B2 | 1/2005 | Ohrbom et al. |
| 7,771,711 | B2 | 8/2010 | Barenholz et al. |
| 2006/0252717 | A1 | 11/2006 | Barenholz et al. |
| 2007/0264273 | A1 | 11/2007 | Barenholz et al. |
| 2008/0112917 | A1 | 5/2008 | Barenholz et al. |

FOREIGN PATENT DOCUMENTS

| | | |
|---|---|---|
| WO | 9216236 A1 | 10/1992 |
| WO | 2004110980 A1 | 12/2004 |

OTHER PUBLICATIONS

Yoshida, M. et al, "Novel Methodologies for the Synthesis of Cyclic Carbonates", Chem. Eur. J. 10:2886-2893 (2004).
Clements JH. Ind. Eng. Chem. res. 42:663-674 (2003).
Greg. T. Hermanson, Bioconjugates Techniques, Academic Press, 1996, pp. 142-143 and 183-185.
International Search Report published Nov. 10, 2009 for PCT/IL2008/000651, filed May 11, 2008.
International Preliminary Report on Patentability published Nov. 10, 2009 for PCT/IL2008/000651, filed May 11, 2008.
Written Opinion published Nov. 9, 2009 for PCT/IL2008/000651, filed May 11, 2008.

*Primary Examiner* — Robert Havlin
(74) *Attorney, Agent, or Firm* — Fleit Gibbons Gutman Bongini & Bianco PL; Martin Fleit; Paul D. Bianco

(57) ABSTRACT

The present disclosure provides processes for the preparation of lipid conjugated cyclic carbonate derivatives. More specifically, the present disclosure is based on the finding that reacting lipids, such as, ceramides, with N,N'-disuccinimidyl derivative, resulted in the formation of, isolatable, substituted cyclic [1,3]-dioxan-2-one and [1,3]-dioxan-2-thione compounds. These isolatable cyclic substituted compounds and derivatives thereof may be used for various applications, such as in vaccination.

16 Claims, 8 Drawing Sheets

(IVa')

(IVb')

(IVa")

(IVb")

LIPID CONJUGATED CYCLIC CARBONATE DERIVATIVES, THEIR SYNTHESIS, AND USES

CROSS-REFERENCE TO RELATED APPLICATIONS

This application is a U.S. national stage application of International Application No. PCT/IL2008/000651, filed May 11, 2008, which designated the United States and which claims priority of U.S. Provisional Patent application No. 60/916,891, filed May 9, 2007.

FIELD OF THE INVENTION

The invention relates to cyclic carbonates and derivatives thereof and in particular to 4,5-substituted-[1,3]-dioxan-2-one or 4,5-substituted-[1,3]-dioxan-2-thione derivatives, their synthesis and different uses thereof.

BACKGROUND OF THE INVENTION

Cyclic carbonates are attractive and important compounds in a variety of fields. Their favorable characteristics include high solubility, high boiling and flash points, low odor levels and evaporation rates, low toxicities, and biodegradability. Cyclic carbonates are found useful as intermediates in organic synthesis, e.g. protection of 1,2- and 1,3-diols and the construction of structurally complex molecules. The alkylene carbonates produced react with aliphatic and aromatic amines, alcohols, thiols, and carboxylic acids. Under certain conditions, they can also undergo ring-opening polymerization.

A number of methods exist to synthesize alkylene carbonates. However, carbon dioxide insertion into the appropriate oxirane is the commercial method employed to synthesize the most common carbonate, [1,3]-dioxolane-2-one. This method includes reaction in the presence of various activating reagents such as alkylammonium halide catalyst (tetraethylammonium bromide) (U.S. Pat. Nos. 2,873,282 and 2,773,070).

It should be noted the synthetic procedures typically involve high pressure of $CO_2$, high reaction temperature, and a stoichiometric amount of activating reagents. In recent years there has been much progress in the synthesis of cyclic carbonates by means of a $CO_2$ fixation process. Acid base catalysts such as $[ZnBr_2(py)_2]$, Mg—Al mixed oxides, and the Cr-salen/DMAP catalyst system, exhibit high activities in the promotion of the reaction of $CO_2$ with epoxide in high efficiency. The palladium-catalyzed reaction of unsaturated alcohols and aryl halides with $CO_2$ can also lead to a variety of cyclic carbonates by means of $CO_2$-elimination/fixation process and shows a high degree of diastereoselectivity, enantioselectivity, and enantiospecificity. Allylic carbonates also transform to the cyclic carbonates in the presence of palladium catalyst by means of a $CO_2$-recycling process (Yoshida M. et al, *Chem. Eur. J.* 10:2886-2893 (2004)).

It has also been shown that six- or poly membered alkylene carbonates can be synthesized by reacting five-membered carbonates with diols. In this regard, alkylene carbonates can be used in lieu of more traditional reactants such as dialkyl carbonates or phosgene. In such a process, the yield of alkylene carbonate produced is dependent on the boiling point difference between the reactant and byproduct diols (Clements J H. *Ind. Eng. Chem. Res.*, 42:663-674 (2003)).

Finally, U.S. Pat. No. 6,838,530 describe the use of cyclic six-membered ring monomers for polymerization so as to form two or more different multifunctional acrylic materials.

SUMMARY OF THE INVENTION

The present disclosure provides processes for obtaining [1,3]-dioxan-2-one and [1,3]-dioxan-2-thione substituted compounds and uses of same in the preparation of various compounds including amine conjugated lipids and lipid conjugated oxazolines.

In the first aspect disclosed herein there is provided a cyclic compound of the following general formula (I):

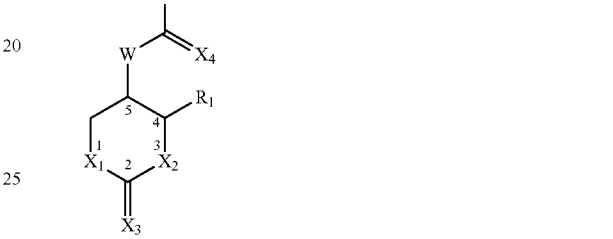

wherein

W represents O, S, NH or $CH_2$;

$X_1$, $X_2$, $X_3$ and $X_4$ represent independently O or S; and $R_1$ and $R_2$ independently represent $C_1$-$C_{24}$ aliphatic moiety which may be saturated or unsaturated, branched or linear chain, the aliphatic moiety may comprise a $C_4$-$C_7$ aliphatic ring portion which may be substituted or non-substituted.

Further provided is a first process for the preparation of a cyclic compound of general formula (I):

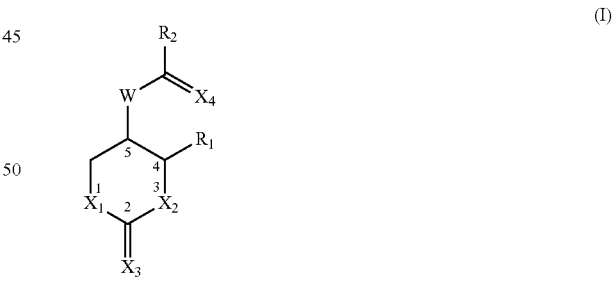

wherein

W represents O, S, NH or $CH_2$;

$X_1$, $X_2$, $X_3$ and $X_4$ represent independently O or S; and $R_1$ and $R_2$ independently represent $C_1$-$C_{24}$ aliphatic moiety which may be saturated or unsaturated, branched or linear chain, the aliphatic moiety may contain a $C_4$-$C_7$ aliphatic ring portion which may be substituted or non-substituted;

the process comprises:

a) providing a lipid of the following general formula (II):

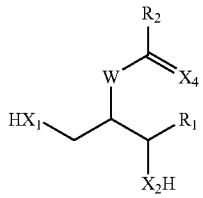

(II)

wherein W, $X_1$, $X_2$, $X_4$, $R_1$ and $R_2$ are as defined above;

b) allowing said lipid of formula (II) to react, in the presence of a basic catalyst, with N,N'-disuccinimidyl derivative of the general formula (III)

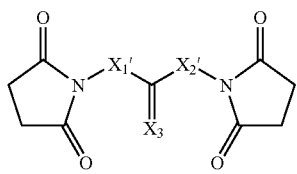

(III)

wherein $X_1'$, $X_2'$ and $X_3$ represent independently O or S, to obtain the cyclic compound of general formula (I).

Further provided by the present disclosure is a compound of general formula (I) as defined hereinabove, obtainable or obtained by the process described above (the said "first process").

In a further aspect disclosed herein there is provided a second process for the preparation of amine conjugated lipids of general formulae (IVa) and (IVb) from the compound of formula (I):

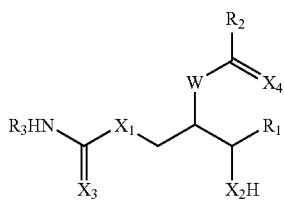

(IVa)

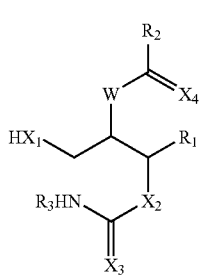

(IVb)

wherein

W represents O, S, NH or $CH_2$;

$X_1$, $X_2$, $X_3$ and $X_4$ represent independently O or S; and $R_1$ and $R_2$ independently represent $C_1$-$C_{24}$ aliphatic moiety which may be saturated or unsaturated, branched or linear chain, the aliphatic moiety may contain a $C_4$-$C_7$ aliphatic ring portion which may be substituted or unsubstituted or a mixture thereof;

the process comprises:

a) providing a cyclic compound of general formula (I) as defined herein above;

b) reacting, under basic conditions, said cyclic compound of formula (I) with a compound comprising at least one primary amine and having the general formula (V):

$NH_2R_3$  (V)

wherein $R_3$ represents a hydrogen, a branched or linear alkyl, alkenyl, alkynyl, aryl, alkaryl or $R_3$ represents a branched or linear polyalkylamine or polyalkenylamine of the formula —$[R_4$—$NR_3]_n$—, wherein $R_4$ represents $C_1$-$C_4$ alkyl or $C_1$-$C_4$ alkenyl; said $R_3$ or each alkylamine unit, —$[R_4NR_3]$—, may be the same or different in said polyalkylamine or polyalkenylamine; and n represents an integer from 1 to 10;

thereby obtaining the amine conjugated lipid of formula (IVa), of formula (IVb) or a mixture of same.

In a further embodiment disclosed herein, step (b) of the said second process comprises the inclusion of a catalyst.

It is noted that the product(s) of the second process, namely, compounds of formulae (IVa) and/or (IVb), may be reacted with a compound of formula (III), as defined above, in a manner similar to the process steps described with respect to the first process followed by a reaction with a compound of formula (V) as described in the second process. To this end, the amine functional groups of the product(s) of the second process are preferably, a priori, protected with a suitable amine-protecting group. This embodiment will be further discussed hereinbelow.

Also provided is a third process, being a process for the separation between an amine conjugated lipid of formula (IVa) and an amine-conjugated lipid of formula (IVb) from a mixture thereof, this ("third") process comprises:

a) reacting at least one functional group on at least one of the amine-conjugated lipid of formulae (IVa) and (IVb) with a modifier to obtain a reaction product comprising a modified amine-conjugated lipid (IVa'), a modified amine-conjugated lipid (IVb') or a combination of a modified amine-conjugated lipid (IVa') and a modified amine-conjugated lipid (IVb');

b) separating at least one modified amine-conjugated lipid from the reaction product to obtain a respective separated modified amine-conjugated lipid.

c) removing from the respective separated modified amine-conjugated lipid the modifier to obtain a separated amine-conjugated lipid corresponding to the separated at least one modified amine-conjugated lipid.

The present disclosure further isolated amine conjugated lipids of general formula (IVa) or formula (IVb) or a mixture thereof, obtainable or obtained by the process as described hereinabove or a di-substituted amine conjugated lipid of general formula (VII),

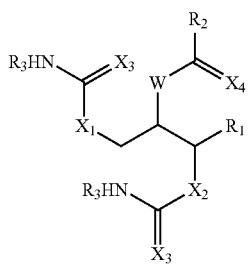

(VII)

obtainable or obtained by the process of the invention.

Also provided by the present disclosure are amine conjugated lipids of general formula (IVa) or formula (IVb) or a mixture thereof, or a di-substituted amine conjugated lipid of general formula (VII) all being obtainable or obtained by the processes disclosed herein.

Yet further provided is a fourth process, the process being for the preparation of a lipid conjugated oxazoline of the following formula (VI):

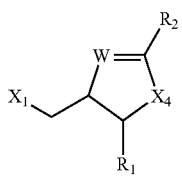

(VI)

wherein
W represents, NH;
$X_1$ and $X_4$ represent independently O or S and
$R_1$ and $R_2$ independently represent $C_1$-$C_{24}$ aliphatic moiety which may be saturated or unsaturated, branched or linear chain, the aliphatic moiety may contain a $C_4$-$C_7$ aliphatic ring portion which may be substituted or unsubstituted;

the (fourth) process comprises:
(a) providing a cyclic compound of general formula (I) as defined herein;
(b) mixing said cyclic compound of formula (I) with an organic solvent to provide a reaction mixture;
(c) heating said reaction mixture to a temperature above 45° C., optionally, in the presence of base, so as to obtain said lipid conjugated oxazoline of formula (VI).

Further disclosed is a lipid conjugated oxazoline of formula (VI) obtainable or obtained by the process as described hereinabove.

Finally, provided are pharmaceutical compositions comprising an amine conjugated lipid of any one of formula (IVa), (IVb), (VII) or a lipid conjugated oxazoline of formula (VI) obtainable or obtained by the processes disclosed herein, or a mixture of same, in combination with a therapeutically active agent.

BRIEF DESCRIPTION OF THE FIGURES

In order to understand the invention and to see how it may be carried out in practice, some embodiments will now be described, by way of non-limiting example only, with reference to the accompanying drawings, in which.

DETAILED DESCRIPTION OF SOME NON-LIMITING EXEMPLARY EMBODIMENTS

Figure 1:
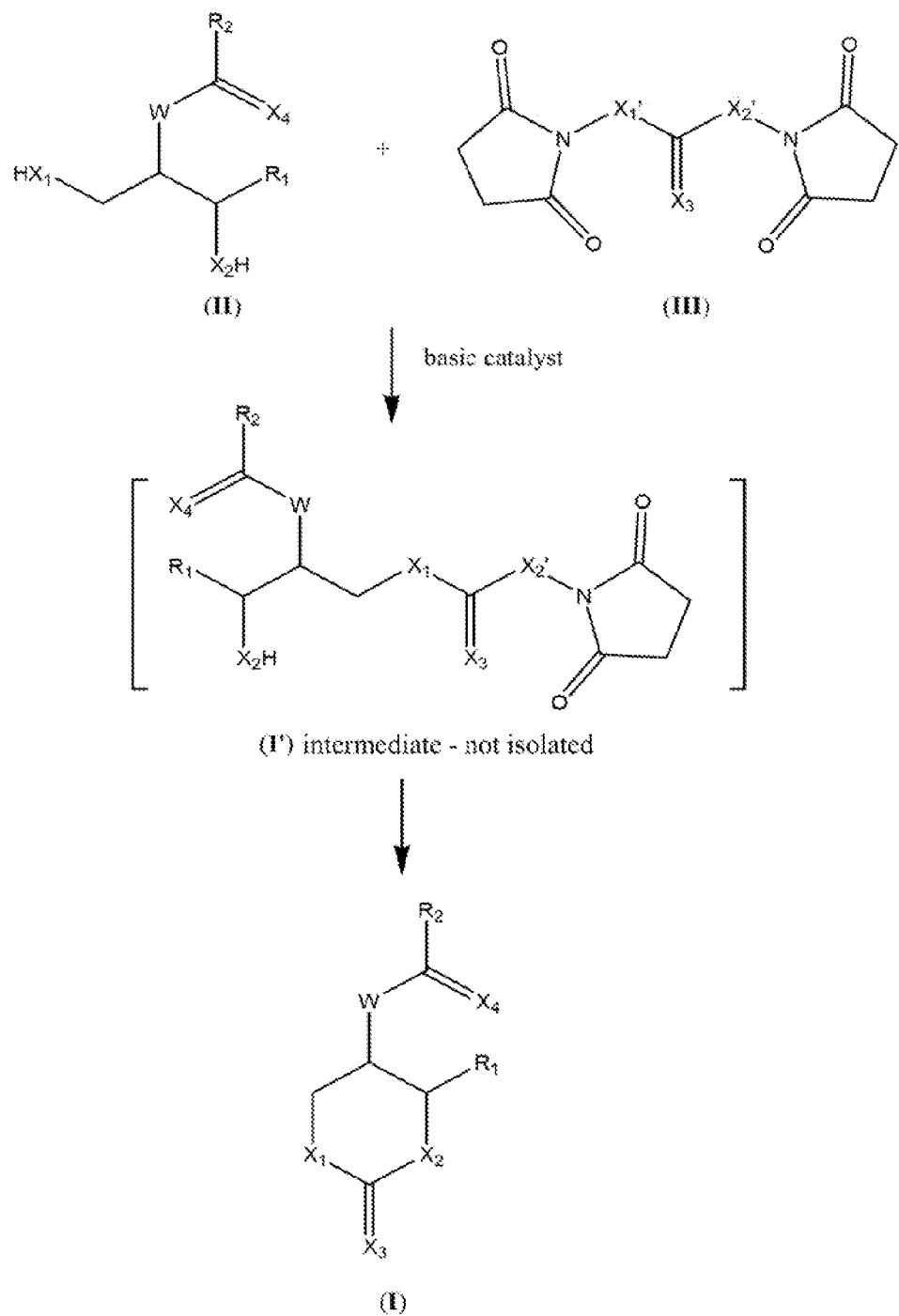
FIG. 1 is a schematic illustration of a process for the preparation of compound (I) in accordance with an embodiment of the invention.

The present invention is based on the finding that reacting lipids, and in particular, ceramides with N,N'-disuccinimidyl derivative results in the formation of an isolatable cyclic [1,3]-dioxan-2-one and [1,3]-dioxan-2-thione substituted compounds. These isolatable cyclic substituted compounds may be used for various applications as detailed and claimed herein.

Thus, in accordance with a first of its aspects, there is provided a cyclic compound of the following general formula (I):

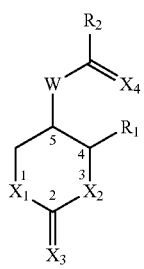

(I)

wherein
W represents O, S, NH or $CH_2$;
$X_1$, $X_2$, $X_3$ and $X_4$ represent independently O or S; and
$R_1$ and $R_2$ independently represent $C_1$-$C_{24}$ aliphatic moiety which may be saturated or unsaturated, branched or linear chain, the aliphatic moiety may comprise a $C_4$-$C_7$ aliphatic ring portion which may be substituted or non-substituted.

In the context of the present disclosure the term "aliphatic moiety" it is to be understood as any saturated (i.e. alkyl) or unsaturated (i.e. alkenyl or alkynyl), non-aromatic, carbon containing compound in which the carbon atoms are joined in a chain to form a hydrocarbon backbone. The carbon atoms in the hydrocarbon backbone may form a linear or branched chain. The aliphatic moiety may also comprise a portion in which the carbon atoms form a closed ring. The closed ring may be saturated or unsaturated. Further, in the context of the present disclosure, the aliphatic moiety may be substituted by heteroatom-comprising groups, such as hydroxyl, thiol, amine, amide, as well as by a saturated, unsaturated or aromatic $C_4$-$C_7$ ring. It is to be understood that in the context of the present invention, the terms "alkyl", "alkenyl" or "alkynyl" denote straight as well as branched chains.

In accordance with one embodiment, $R_1$ and $R_2$ independently represent $C_8$-$C_{24}$ alkyl or $C_8$-$C_{24}$ alkenyl chain. In one preferred embodiment, $R_1$ and $R_2$ independently represent a $C_{12}$-$C_{18}$ alkyl or $C_{12}$-$C_{18}$ alkenyl chain.

In accordance with another embodiment $R_1$ is an alkenyl chain comprising one or more double bonds along the carbohydrate backbone. One non-limiting preferred $R_1$ is an alkenyl chain having at least one double bond. It is to be understood that the at least one double bond may be between any two carbon atoms of the alkenyl chain. In one embodiment the double bond is between the first and second carbon atoms (namely, $C_1$-$C_2$) of the alkenyl chain. A preferred $R_2$ is an alkyl chain. In one embodiment, $R_1$ represents —CH=CH—$C_{13}H_{25}$ and $R_2$ represent —$C_{15}H_{31}$.

In accordance with one embodiment W represents a secondary amine group, i.e.—NH—.

In accordance with a further embodiment, $X_1$, $X_2$, $X_3$ and $X_4$ are identical. When $X_1$, $X_2$, $X_3$ simultaneously represent an oxygen, the compound may be generally termed [1,3]-dioxane-2-one derivative. Similarly, when $X_1$ and $X_2$ represent and oxygen and $X_3$ represent a sulfur atom the compound may be generally termed [1,3]-dioxane-2-thione derivative. In accordance with an embodiment, $X_1$, $X_2$, $X_3$ and $X_4$ represent simultaneously an oxygen atom, i.e. a [1,3]-dioxane-2-one derivative.

It should be emphasized that the compounds and products in accordance with the present disclosure may comprise one or more stereogenic center(s). When these compounds comprise one or more stereogenic center(s), both the (R) and (S) configurations of said stereogenic center(s) are within the scope of the present invention. Preferred stereogenic center(s) are specifically identified hereinafter.

In one embodiment the compound of formula (I) comprises a first stereogenic carbon on position 4 (as marked in the general formula) and a second stereogenic carbon on position 5 (as marked in the general formula). Each stereogenic carbon may be, independently, in the (R) or (S) configuration. Thus, within the scope of this embodiment all possible isomers of compound of formula (I), namely (4R,5S), (4S,5R), (4R,5R) and (4S,5S) isomers are included.

Further, it should be emphasized that when the compounds and products of the invention comprise one or more carbon-carbon double bond(s), both the (E) and (Z) configuration of said carbon-carbon double bond(s) are within the scope of the present invention.

In accordance with one embodiment the compound of formula (I) may comprise one or more carbon-carbon double bond(s) in the (E) or (Z) in the $R_1$ and/or $R_2$ substituents.

A preferred embodiment in accordance with the disclosure provides a compound of formula (I) in which $R_1$ represents —CH=CH—$C_{13}H_{27}$ and $R_2$ represents —$C_{15}H_{31}$. One particular compound in accordance with this embodiment is 5-(hexadecanoylamido)-4-pentadecene-[1,3]-dioxanone-2-one (having W as a secondary amine, and $X_1$, $X_2$, $X_3$ and $X_4$ an oxygen).

A preferred steroisomer of the cyclic compound of the present disclosure is (4R, 5S)-5-(hexadecanoylamido)-4-[(1E)-pentadecene]-[1,3]-dioxanone-2-one (referred to herein as formula (I)):

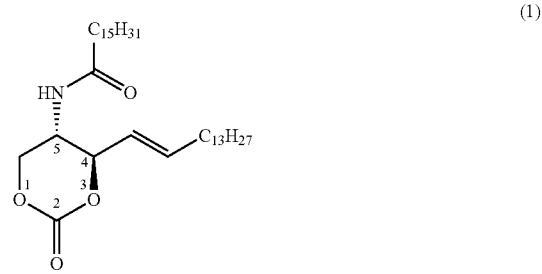

The present disclosure also provides a process for preparing the compound of formula (I). In accordance with the process of the invention, a lipid having the formula (II):

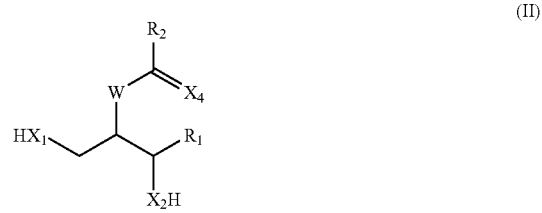

wherein W, $X_1$, $X_2$, $X_4$, $R_1$ and $R_2$ are as defined above is initially reacted with N,N'-disuccinimidyl derivative of the general formula (III):

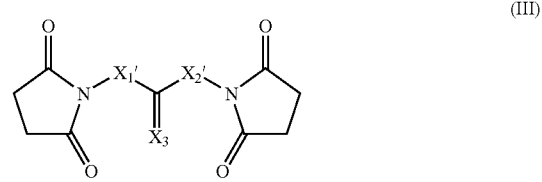

wherein $X_1'$, $X_2'$ and $X_3$ represent, independently, an oxygen or sulfur atom.

The reaction may be carried out in the presence of a basic catalyst.

The term "lipid" in accordance with the present disclosure denotes a wide range of lipids in which fatty acids are linked via amide bonds to a long-chain base such as a sphingosine or sphingoid type of molecule. In the context of the present disclosure a lipid is any molecule having the general formula (II) as defined herein. As evident from the general formula, the lipids are those comprising at least two nucleophilic groups, such as hydroxyl groups. Lipids, in accordance with the present disclosure, comprise ceramides, sphingomyelins, sphingolipid, glycosphingolipids, cerebrosides and gangliosides. Some embodiments of the lipid are further described hereinafter.

The term "amine conjugate" denotes any compound comprising a linkage represented by the general formula —$NHR_i$ ($C=X_i$)—, where i represents an integer for identifying the specific "R" or "X" substituent. The term also may be understood to represent a conjugate comprising an amide linkage (where X is an oxygen atom) or a thioamide (where X is a sulfur atom).

The term "catalyst" denotes any chemical substance that is capable of increasing the rate of reaction between the lipid and N,N'-disuccinimidyl derivative, without being consumed or between the product of the reaction between the lipid and the N,N'-disuccinimidyl derivative, i.e. between the cyclic compound of formula (I) and amine compound of general formula (V) as will be discussed in detailed hereinbelow. The catalyst may allow the reaction to be conducted in a quicker than that conducted in the absence of the catalyst and at lower temperatures. In the context of the present disclosure the catalysts promotes the nucleophilic attack of the lipid on the carbonyl of the N,N'-disuccinimidyl derivative. This nucleophilic attack may also be regarded as acylation catalyst, promoting the acylation of the lipid. A non-limiting list of basic catalyst in accordance with the present disclosure comprises dimethylaminopyridine (DMAP), an imidazole derivative (tetrazole, dicyanoimidazole) or diisopropylethylamine. Other basic catalysts may be found in the literature [e.g. in Greg T. Hermanson *Bioconjugate Techniques*, Academic Press 1996 pp 142, 183].

The general synthetic process is illustrated in FIG. 1. Without being bound by theory, it is believed that a reaction between a lipid of formula (II) with the N,N'-disuccinimidyl derivative (III) initially forms an intermediate (I') which is converted to the cyclic compound of formula (I).

In a preferred embodiment the lipid is an N-acyl sphingosine. A non-limiting group of N-acyl sphingosine comprise, without being limited thereto, ceramides. The term "ceramides" denoted lipids which contain a fatty acid chain attached trough an amide linkage to a sphingosine. In one embodiment, the ceramides are $C_2$ to $C_{24}$ ceramides. A preferred group of ceramides are $C_8$ to $C_{24}$ ceramide, $C_8$ to $C_{24}$ dihydroceramides, $C_8$ to $C_{24}$ phytoceramides, $C_8$ to $C_{24}$ dihydrophytoceramides, $C_8$ to $C_{24}$ ceramine, $C_8$ to $C_{24}$ dihydroceramine, $C_8$ to $C_{24}$ phytoceramine and $C_8$ to $C_{24}$ dihydrophytoceramines.

Figure 2:
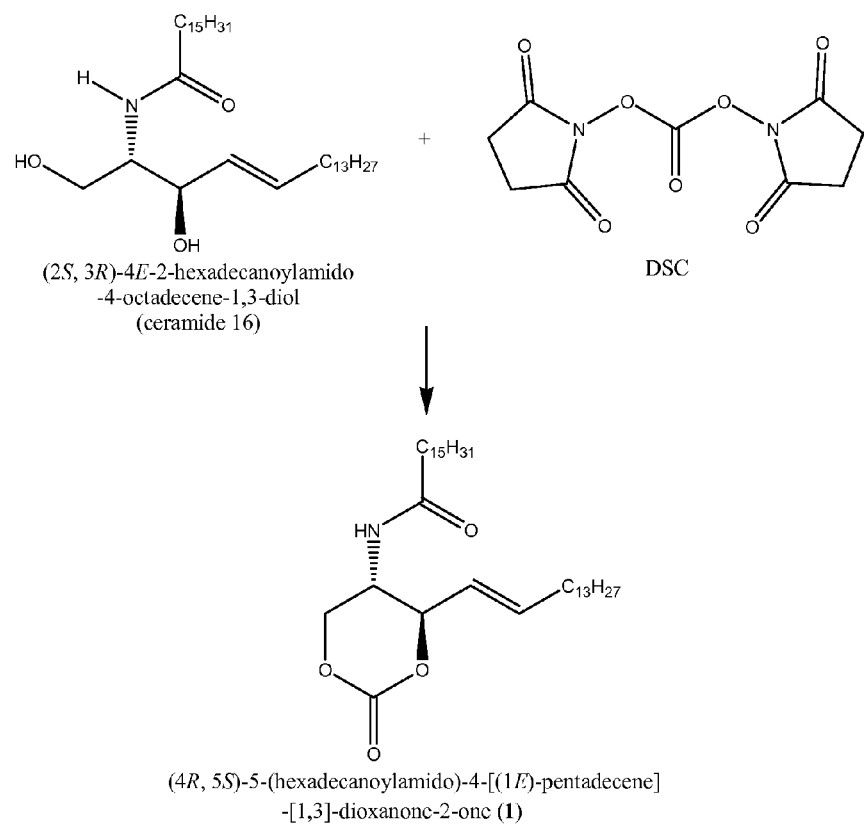
FIG. 2 is a schematic illustration of a process for the preparation of (4R,5S)-5-(hexadecanoylamido)-4-[(1E)-pentadecene]-[1,3]-dioxane-2-one (1) in accordance with another embodiment of the invention.

Thus, when the lipid is a ceramide, a preferred compound of the present disclosure is (4R,5S)-5-(hexadecanoylamido)-4-[(1E)-pentadecene]-[1,3]-dioxanone-2-one (1). The (4R,5S)-5-(hexadecanoylamido)-4-[(1E)-pentadecene]-[1,3]-dioxanone-2-one is obtainable by a process as illustrated in FIG. 2. As clearly shown, $C_{16}$-ceramide is reacted with N,N'-disuccinimidyl (DSC) in the presence of DMAP to form said specific compound of formula (1).

Figure 3:
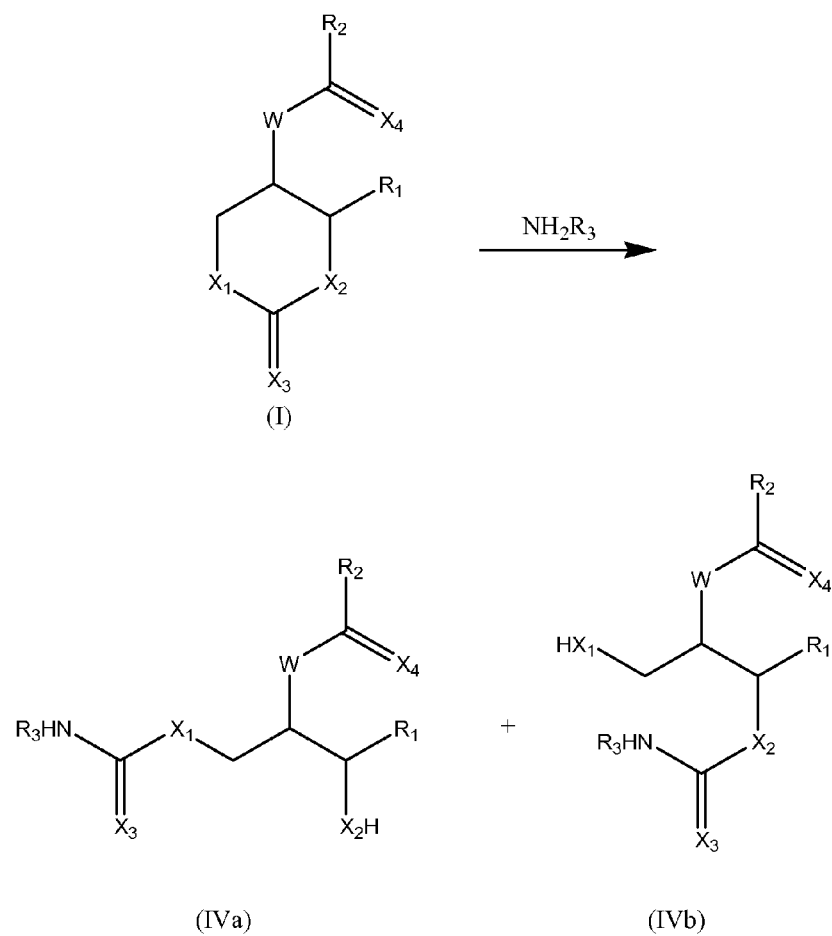
FIG. 3 is a schematic illustration of a process for the preparation of the amine conjugated lipids of formulae (IVa) or (IVb) in accordance with yet another embodiment of the invention.

There are various applications for the cyclic compounds disclosed herein. The cyclic compounds of formula (I) comprise a cyclic carbonyl carbon atom. In addition, the cyclic compounds of formula (I) comprise two good leaving groups, resulting in the cleavage of one of the two unsymmetrical $X_1/X_2$-carbon bonds of the carbonate ring. Thus, upon reacting the cyclic compounds disclosed herein with an amine of the formula $NH_2R_3$, two amine-conjugated lipid regioisomers may be produced. The general reaction of the cyclic compound of formula (I) with $NH_2R_3$ is illustrated in FIG. 3. Formulae (IVa) and (IVb) represent the two amine conjugated lipid obtained by this process. These two amine conjugated lipids are regioisomers and therefore may possess close or identical physical characteristics such as melting and boiling points, molecular weight etc.

The term "regioisomer" denotes a product of a regioselective reaction wherein there is more than one direction of chemical bond to be formed or broken in a chemical reaction, such as a nucleophilic attack. While at times, there is preference to one direction of a chemical bond, thereby producing two regioisomers in a certain ratio between them, the present invention also encompass chemical reactions in which the two regioisomers are formed at equal amounts, i.e. at a 1:1 ratio. The ratio between the regioisomers may depend on various reaction conditions, such as temperature, solvent, concentration, relative excess of amine etc.

Also provided herein is a process for the preparation of an amine conjugated lipid of general formulae (IVa) and (IVb):

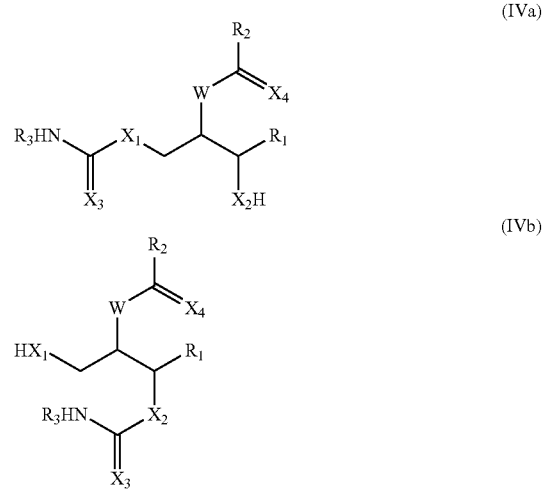

wherein
W represents O, S, NH or $CH_2$;
$X_1$, $X_2$, $X_3$ and $X_4$ represent independently O or S; and
$R_1$ and $R_2$ independently represent $C_1$-$C_{24}$ aliphatic moiety which may be saturated or unsaturated, branched or linear chain, the aliphatic moiety may contain a $C_4$-$C_2$ aliphatic ring portion which may be substituted or unsubstituted or a mixture thereof;

the process comprises:
a) providing a cyclic compound of the general formula (I) as defined hereinabove;
b) reacting under basic conditions said cyclic compound of the general formula (I) with a compound comprising at least one primary amine of the general formula (V):

$$NH_2R_3 \qquad (V)$$

wherein $R_3$ represents a hydrogen, a branched or linear alkyl, alkenyl, alkynyl, aryl, alkaryl; or $R_3$ represents a branched or linear polyalkylamine or polyalkenylamine of the formula $—[R_4—NR_3]_n—$, wherein $R_4$ represents $C_1$-$C_4$ alkyl or $C_1$-$C_4$ alkenyl; said $R_3$ or each alkylamine unit, $—[R_4NR_3]—$, may be the same or different in said polyalkylamine or polyalkenylamine; and
n represents an integer from 1 to 10.

In one embodiment the reaction of the cyclic compound of the general formula (I) with the compound general formula (V) is conducted in the presence of a catalyst. In a further embodiment a mixture of amine conjugated lipids of formula (IVa) and of formula (IVb) is obtained.

It should be understood that the invention also encompasses any mixture of amine conjugated lipids of formula (IVa) and (IVb) obtainable or obtained by the process disclosed herein, wherein one amine conjugated lipid may be the main product, i.e. quantitatively, produced in an amount higher than the corresponding amine conjugated lipid or they may be produced in equal amounts depending on the reaction conditions and the starting material used.

The amine, $NH_2R_3$, used in process of the ring opening could be a primary amine, wherein $R_3$ represents a hydrogen, a branched or linear alkyl, alkenyl, alkynyl, aryl, alkaryl; or $R_3$ may represents a branched or linear polyalkylamine or polyalkenylamine of the formula $—[R_4—NR_3]_n—$, wherein said $R_4$ is preferably, however, not exclusively, a $C_1$-$C_4$ alkyl or $C_2$-$C_4$ alkenyl, each alkylamine unit $R_4NR_3—$ may be the same or different in said polyalkylamine or polyalkenylamine; and n represents an integer from 1 to 10. Preferably, however, not exclusively, the alkyl is $C_1$-$C_4$ alkyl and the alkenyl, alkynyl, $C_2$-$C_4$, respectively and aryl, alkaryl are $C_5$-$C_{10}$.

Figure 4:
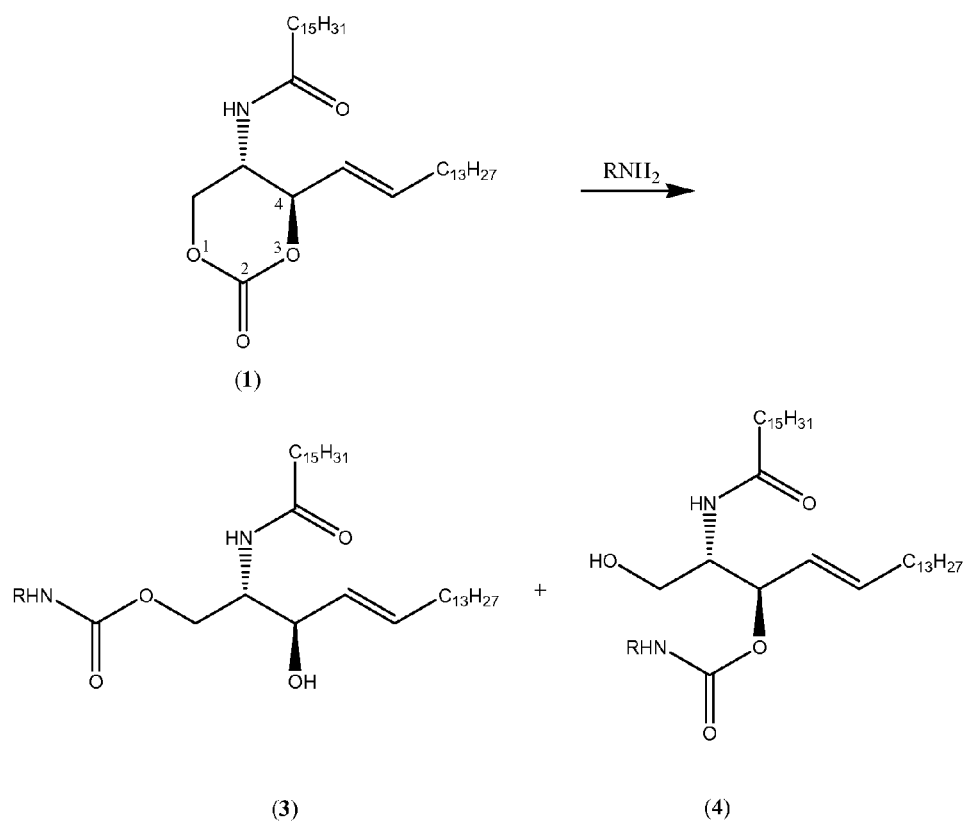
FIG. 4 is a schematic illustration of a process for the preparation of the amine conjugated lipids (3) and (4) from compound (I), in accordance with a further embodiment of the invention.
Figure 5A:
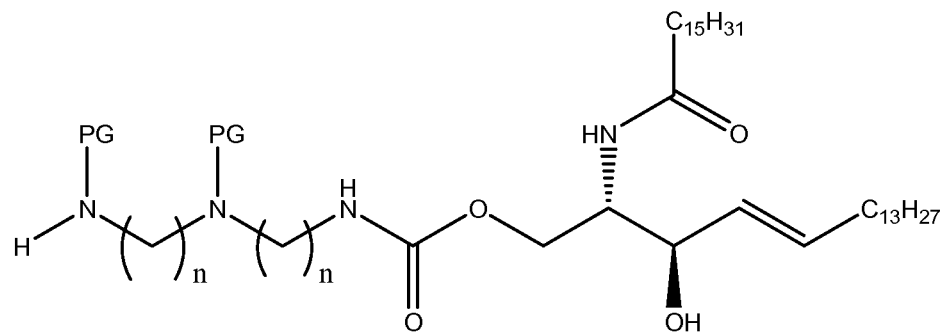
FIG. 5A-5B is a schematic representation of the modified amine-conjugated lipid of formulae (IVa') and (IVb') (FIG. 5A) and non-modified amine-conjugated lipid of formulae (IVa") and (IVb") (FIG. 5B).
Figure 5A:
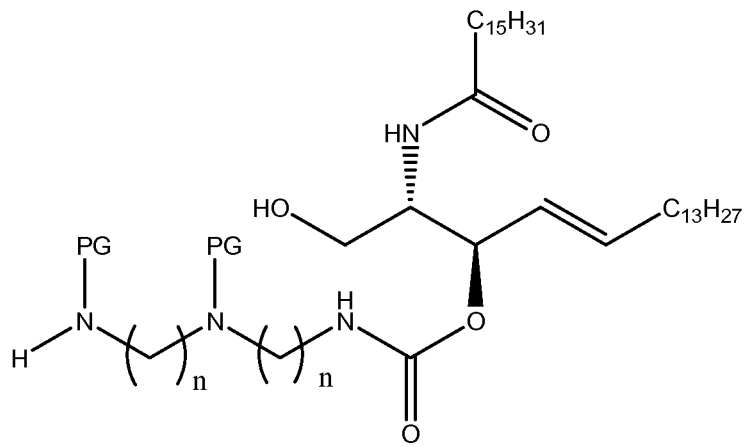
Figure 5B:
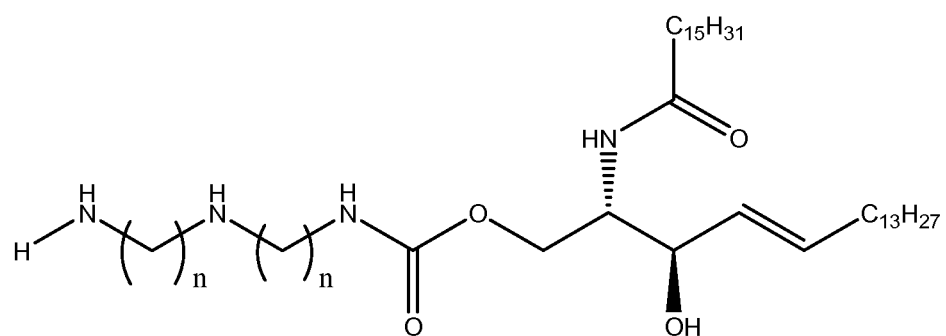
Figure 5B:
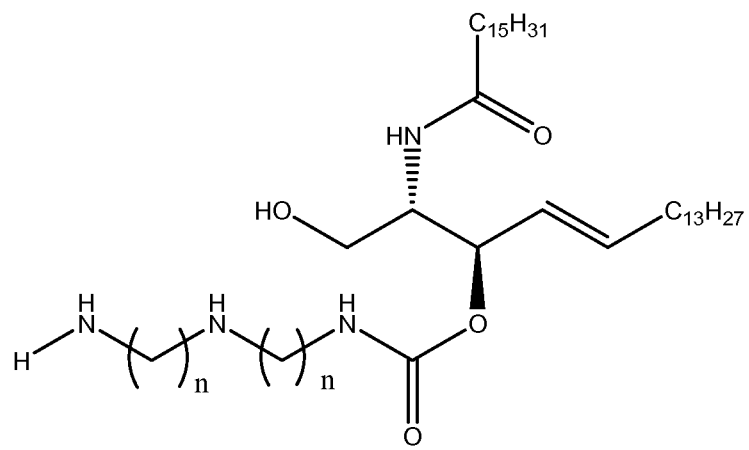

Specifically, in the reaction of the hexadecanoic acid (2-oxo-4-pentadec-1-enyl-[1,3]-dioxan-5-yl)-amide (1) with amine containing compounds, two amine conjugated lipids (i.e. two regioisomers) are formed, as illustrated in the FIG. 4. This schematic illustration shows an amine compound $NH_2R_3$, where $R_3$ may be any carbon containing atom as defined herein, reacts with the hexadecanoic acid (2-oxo-4-pentadec-1-enyl-[1,3]dioxan-5-yl)-amide (1) and producing a mixture of two regioisomers, the first resulting from the cleavage of the cyclic carbonate ring at position 1 (isomer (3)), the second resulting from the cleavage of the cyclic carbonate ring at position 3 (isomer (4)).

Separation between the two regioisomers exploits the existence of functional groups in the said compounds. A "functional group" may be defined as a certain arrangement of atoms within molecules, that are responsible for the chemical characterization of the molecule with respect to its physical properties and the possible reactions it may undergo. Examples of functional groups may include, without being limited thereto, amine, amide, hydroxyl, carboxyl, ester, ether, sulfoxide, sulfide or thiol as well as others. The functional groups may be primary functional groups as well as secondary functional groups. According to one embodiment, the functional group is an amine functional group.

Thus, in accordance with one aspect disclosed herein there is provided a separation process between amine conjugated lipid (IVa) and amine conjugated lipid (IVb) comprises:
a) reacting at least one functional group on at least one of the amine-conjugated lipid of formulae (IVa) and (IVb) with a modifier to obtain a reaction product comprising a modified amine-conjugated lipid (IVa'), a modified amine-conjugated lipid (IVb') or a combination of a modified amine-conjugated lipid (IVa') and a modified amine-conjugated lipid (IVb');
b) separating at least one modified amine-conjugated lipid from the reaction product to obtain a respective separated modified amine-conjugated lipid.
c) removing from the respective separated modified amine-conjugated lipid the modifier to obtain a separated amine-conjugated lipid corresponding to at least one modified amine-conjugated lipid.

One example of a modified amine-conjugated lipid of formula (IVa) and (IVb) and wherein an amine functional group is in the modified and non-modified form, is provided in FIG. 5. These amine modified compound are designated as compounds (IVa') and (IVb') (FIG. 5A) respectively and the unmodified are designated (IVa") and (IVb") (FIG. 5B), respectively. In this specific example of modified amine conjugated lipids, $X_1$, $X_2$, $X_3$ and $X_4$ represent an oxygen, W represents $—NH—$, $R_1$ represents $—CH=CH—C_{13}H_{27}$, $R_2$ represents $C_{15}H_{31}$ and $R_3$ represents any alkylamine moiety modified with a protecting group denoted PG shown in FIG. 5A-5B.

In accordance with an alternative or additional embodiment, it is noted that also the modification may take place on one of the $X_1$ or $X_2$ groups. For example, $X_1$ and $X_2$ may represent independently oxygen, and the modifier may be, for example, O-trityl.

The term "modifier" denotes a group which is introduced into a molecule by the chemical modification of a functional/reactive group in a compound of interest for the purpose of obtaining a new derivative of the molecule with different physical/chemical properties so as to enable the isolation of the modified molecule from non-modified or otherwise modified molecules. The "modifier" may be a bulky group, a conventionally used protecting group (groups known to be introduced into a molecule for the purpose of preventing the uncontrolled modification/alteration of a functional group in subsequent chemical reactions), or any other group that may be reacted with a functional group in a molecule and later removed/cleaved from that functional group. There are various modifiers and protecting groups known to those skilled in the art and may be categorized by the type of functional group they intend to protect.

In accordance with one embodiment, the modifier is such that it is capable of reacting and thereby protecting a functional group in the molecule Amine protecting groups may include, without being limited thereto, carbobenzyloxy (Cbz), tert-butyloxycarbonyl (BOC), 9-Fluorenylmethyloxycarbonyl (FMOC), benzyl; carbonyl protecting groups such as acetals, ketals, acylals, dithianes; carboxylic acid protecting groups such as methyl esters, benzyl esters, tert-butyl esters, silyl esters. Alcohol protecting groups include, without being limited thereto acetyl, O-trityl, trifluoroacetamide, dialkyl Phosphoramidates, tetrahydropyran, methoxymethylether, β-methoxyethoxymethyl ether (MEM), p-methoxybenzyl ether (PMB), methylthiomethyl ether, pivaloyl (PIV), silyl ether, trimethylsilyl (TMS), tert-butyldimethylsilyl (TBDMS), and triisopropylsilyl (TIPS) ethers). Other protecting groups may be found in the literature [e.g. in Theodora W. Greene and Peter G. M. Wuts, *Protective Groups in Organic Synthesis*, 2nd Edition, 1991 John Wiley & Sons, Inc. pp 309].

Once the two regioisomers are chemically modified (one or both, as described above) they can be separated by known separation techniques.

"Separation techniques" are meant to include any chemical procedure utilizing the different physical characteristics of compounds in a mixture so as to permit the separation therebetween. Non-limiting list of these techniques comprise distillation, GC-chromatography, HPLC-chromatography, extraction, precipitation etc.

Following separation, the protecting groups are removed (either in a single or multi step cleavage process) to obtain an isolated amine conjugated lipid of formula (IVa) and an isolated amine conjugated lipid of formula (IVb). Removal of the protecting group(s) may be achieved by hydrochloric acid, whether diluted or concentrated, trifluoroacetic acid in solution in dichloromethane or neat, hydrogenolysis, piperidine or other suitable methods for removing amino protecting groups.

In one embodiment disclosed herein the process of separating may also comprise the following steps:
(b1) reacting a separated modified amine-conjugated lipid (IVa') and/or (IVb') with a N,N'-disuccinimidyl derivative of the general formula (III)

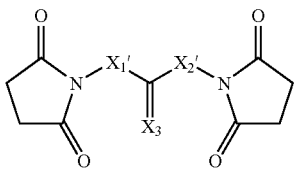

(III)

wherein $X_1'$, $X_2'$ and $X_3$ represent independently O or S; to obtain a succinyl carbonate-modified amine-conjugated lipid (VIb') and/or (VIa');

(b2) reacting the succinyl carbonate-modified amine-conjugated lipid with a primary amine of the general formula (V):

$$NH_2R_3 \quad (V)$$

wherein $R_3$, is as defined, and may be the same or different from $R_3$ in said separated modified amine-conjugated lipid to obtain disubstituted modified amine conjugated lipid (VII').

The present invention further envisages an amine conjugated lipid of general formulae (IVa) or (IVb), or mixtures thereof obtained by a process as described hereinabove or a di-substituted amine conjugated lipid of general formula (VII),

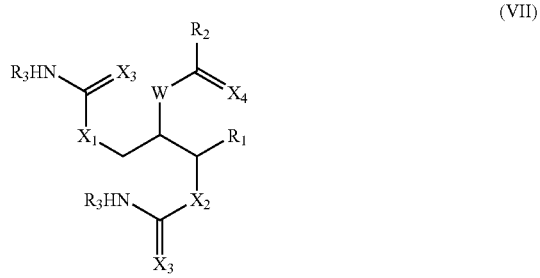

(VII)

obtainable or obtained by the process described hereinabove and below.

In a further aspect there is provides an isolated amine-conjugated lipid of general formulae (IVa) or (IVb) obtainable or obtained by the process as described hereinabove or a di-substituted amine conjugated lipid of general formula (VII),

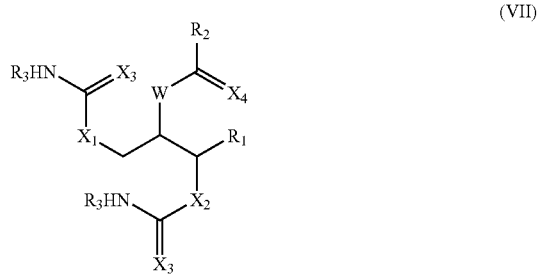

(VII)

obtainable or obtained by the process as described hereinabove and below.

Figure 6A:
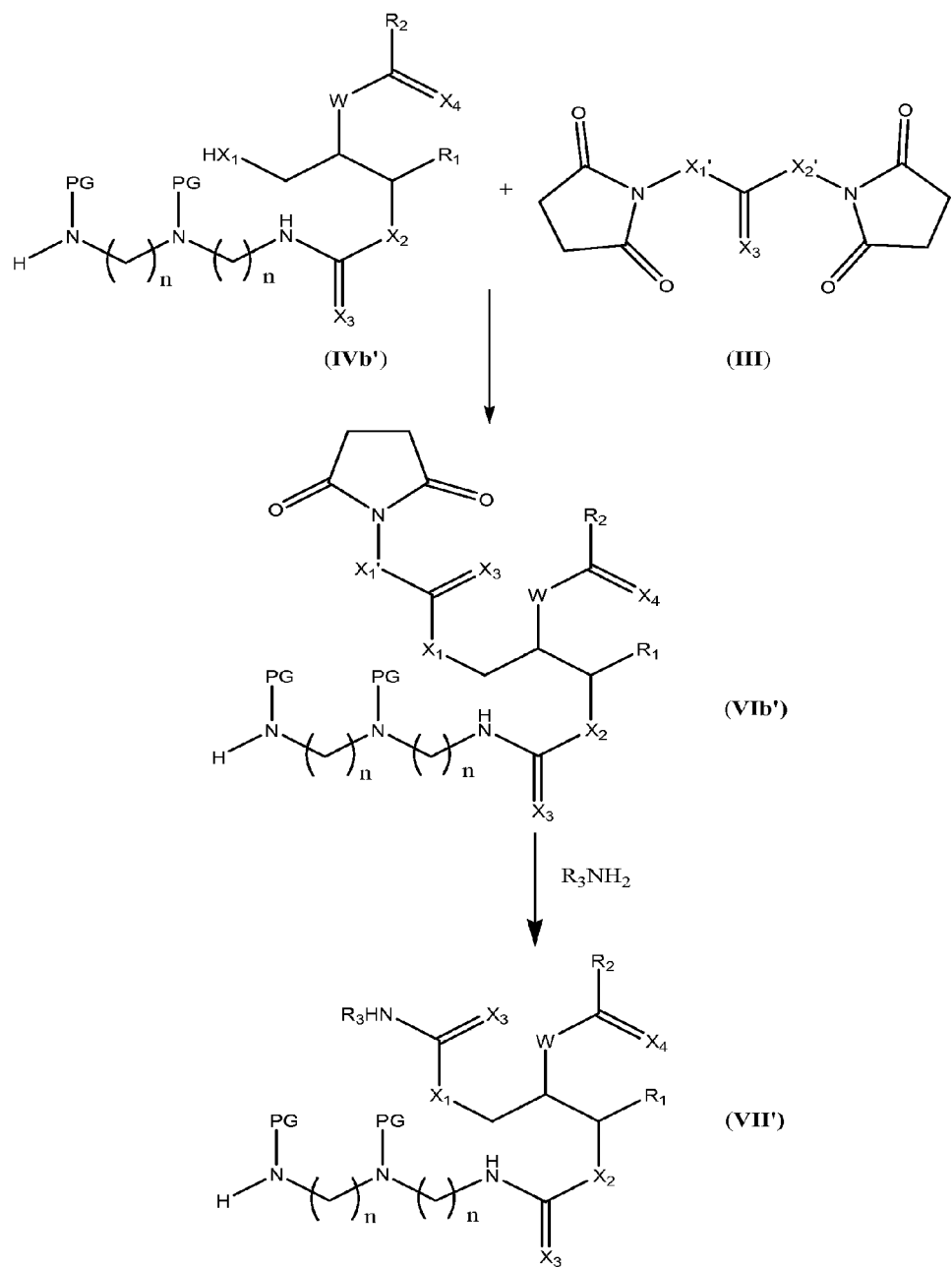
FIGS. 6A-6B are a schematic representation of a process for providing a lipid conjugated to two polyamine moieties, in accordance with an embodiment of the invention (FIG. 6A) and a specific disubstituted polyalkylamine conjugated lipid in accordance with one embodiment of the invention (FIG. 6B).
Figure 6B:
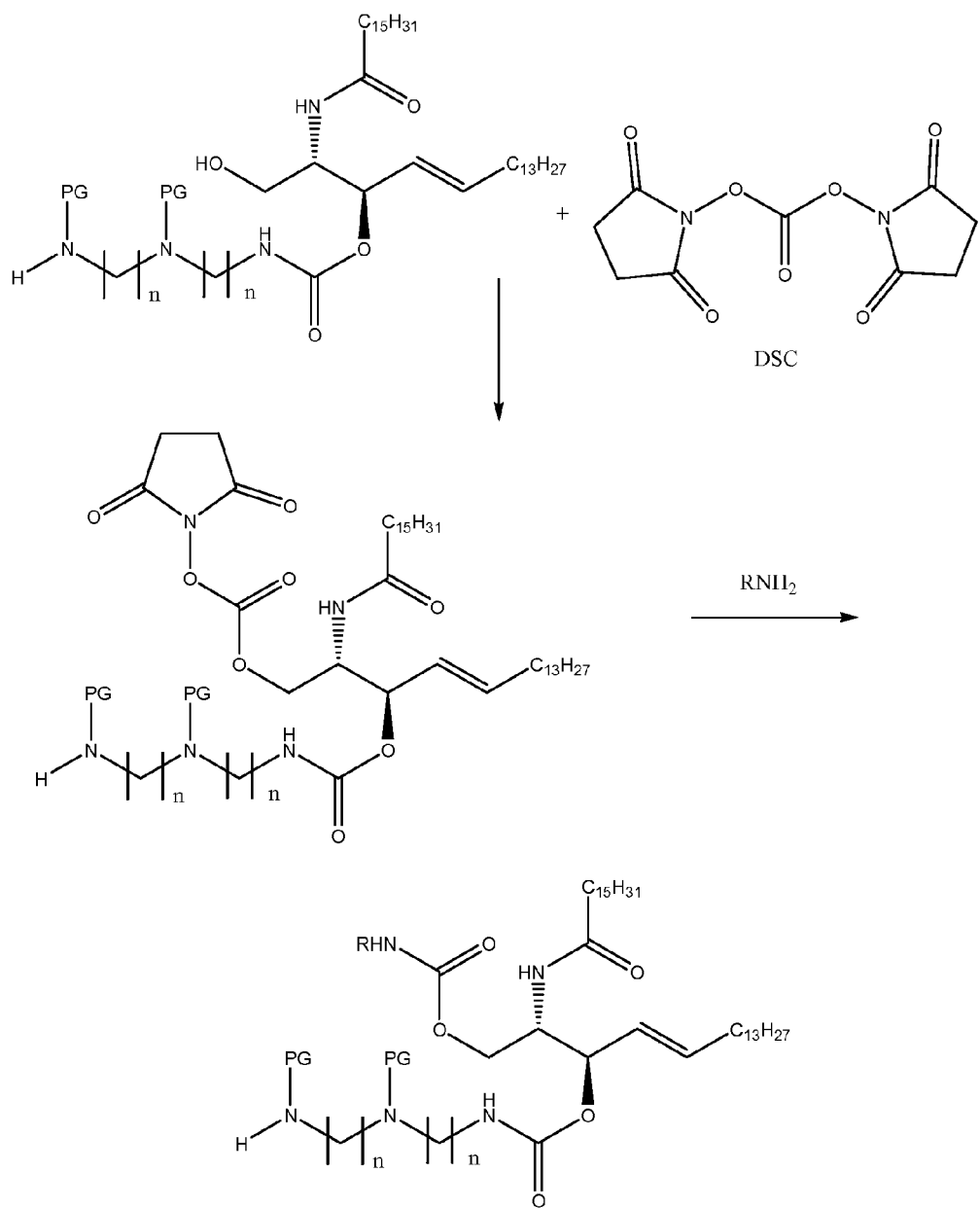

It is noted that in a similar procedure as will be described hereinbelow, a disubstituted amine-conjugated lipid may be prepared. FIGS. 6A-6B is a schematic illustration of the process steps for obtaining the disubstituted derivative from the amine conjugated lipid (IVb'). It is noted that similarly, the disubstituted derivative from amine conjugated lipid (IVa) may be obtained, mutatis mutandis.

As illustrated, and as a first step, the amine modified conjugated lipid of formula (IVb') is reacted with DSC to produce a succinyl carbonate-modified derivative represented by the general formula (VIb'). Again, as noted above, the same first step may be performed with amine conjugated lipid (IVa). In the presence of a primary amine (V), the succinyl moiety is then substituted thereby to form a modified disubstituted amine conjugated lipid of formula (VII'). It is noted that the primary amine (V) replacing the succinyl moiety may be the same or different from that introduced in the second process, so as to form the conjugate of formula (IVb) (or IVa, if that being the amine conjugate used). As a final step, the modifier may be removed from the modified conjugated lipid of formula (VII') to provide the unmodified (i.e. deprotected) disubstituted amine conjugated lipid of formula (VII). This may be achieved by the same procedure described in the third process described above (not shown in FIG. 6A-6B).

When the primary amine (V) replacing the succinyl moiety is different from that introduced in the second process, the amine conjugated lipid (IVa) or amine conjugated lipid (IVb) may result in two different disubstituted amine conjugated lipid.

The two regioisomers obtainable from the opening of the cyclic compound of formula (I), such as the amine conjugated lipids formulae (IVa) and (IVb) have a lipid-like character and thus may be of beneficial effect in therapy. For example, the isolated amine conjugated lipids (IVa) or (IVb) or the mixture of the regioisomers may form part of lipid assemblies including micelles and liposomes.

For the formation of lipid assemblies the one or more regioisomers may be combined with other lipids (liposome forming lipids as well as non-liposome forming lipids), such as DOPE, cholesterol and/or others, at different mole ratios to the lipid like regioisomer(s).

The formed lipid assemblies may be shaped as unsized heterogeneous and heterolamellar vesicles (UHV) having a diameter of about 50-5000 nm. The formed UHV, may be downsized to form small unilamellar vesicles (SUV) and/or converted to large (more homoegenous) unilamellar vesicles (LUV) having a diameter of about 50-100 nm or to large multivesicular vesicles (LMVV). The structure and dimensions of the lipid assemblies (e.g. vesicles), e.g. their shape and size may have important implications on their efficiency as vehicles for delivery of the active biological entities to the target, i.e. these determine their transfection properties. Thus the structure of the formed vesicles, UHV (unsized heterogeneous) or LUV (large unilamellar), LMVV (large multivesicular vesicles), OLV (oligolamellar) and MLV (large multilamellar), is one important factor.

Thus, in accordance with one embodiment, the regioisomer, either a single isomer or a mixture of the isomers may be utilized as part of a delivery device for facilitating intracellular transfers of active substances/agents (e.g. for delivery of nucleic acid sequences and the like, e.g. for gene therapy). Thus provided are pharmaceutical compositions comprising an active agent and the isolated regioisomer of formula (IVb) or a mixture of amine conjugated lipids of formulae (IVa) and (IVb). The active agent may be any low or high molecular weight, synthetic, semi synthetic or naturally occurring biological compound which has a beneficial biochemical effect within the body. Efficiency of lipid assemblies comprising the regioisomers of the invention in delivery of an active agent may be determined through biological activity.

One specific example of efficient use of the regioisomers in accordance with the present disclosure is in oligonucleotide transfer into cells (e.g. into cancerous cells). One approach in cancer treatment is to target specified poly- or oligo-nucleotides in the form of antisense in order to interfere with cancer cell function. Transfection with a regioisomer in accordance with the invention may facilitate, for example, vaccination or introduction of genes into cells for their expression, e.g. oligo- and poly-nucleotide therapy.

Another use of regioisomers in accordance with the present disclosure is in the field of vaccination. Accordingly, antigens may be complexed (either encapsulated within the regioisomer(s), entrapped in the lipid-like layer, associated at the surface of the vehicle etc., or mere complexation) with the regioisomer(s) to form an antigenic entity (a vaccine). The complex may further include immunostimulants or any other biologically active agents facilitating the desired modulation (stimulation, enhancement etc.) of the immune response.

Further, the active agent may be an antibody (IgM, IgD, IgA, and IgG antibody etc.), including polyclonal antibodies or monoclonal antibodies, as well as whole antibodies or fragments of the antibodies comprising the antigen-binding domain of the anti-variant product antibodies, e.g. scFv, Fab, F(ab')2, other antibodies without the Fc portion, biseptic antibodies, diabodies, single chain antibodies, other fragments consisting of essentially only the variable, antigen-binding domain of the antibody, etc.

Such pharmaceutical compositions may be prepared for, e.g. intravenous, subcutaneous, topical, intranasal, oral, ocular or intramuscular in vivo administration as well as ex vivo and in vitro (cell culture) applications.

The physiologically acceptable carrier according to the invention generally refers to inert, non-toxic solid or liquid substances preferably not reacting with the biologically active molecule or with the conjugate and which is required for the effective delivery of the conjugate with the biologically active molecule. The assemblies forming part of the composition of the invention are typically in the form of suspensions or dispersions.

Non-limiting examples of physiologically acceptable carrier include water, saline, 5% dextrose (glucose), 10% sucrose etc., either alone or with minor amounts (up to 10%) of an alcohol, such as ethanol The cyclic compound of formula (I) may be further utilized for the preparation of lipid conjugated oxazoline of the following formula (VI):

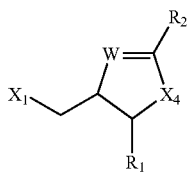

(VI)

wherein W, $X_1$ and $X_4$, $R_1$ and $R_2$ are as defined hereinabove with respect to compound (I).

The preparation process of such a lipid conjugated oxazoline may comprise mixing the cyclic compound of formula (I) with an organic solvent, preferably, albeit, not exclusively, a non-polar organic solvent. The reaction mixture may then be heated to a temperature above 45° C., thereby forming said lipid conjugated oxazoline of formula (VI). The non-polar organic solvent could be selected from but is not limited to hexane, cyclohexane, iso-octane, THF.

Also disclosed is a lipid conjugated oxazoline of formula (VI) obtainable by the process of the invention as herein described above.

In another aspect there is provided a pharmaceutical composition comprising a lipid conjugated oxazoline of formula (VI).

In yet one other aspect there is provided a pharmaceutical composition comprising an amine conjugated lipid of any one of formulae (IVa), (IVb), and (VII) or a mixture thereof obtainable by the process disclosed herein, in combination with a therapeutically active agent.

DESCRIPTION OF NON-LIMITING PREFERRED EXAMPLES

Example 1

Synthesis of hexadecanoic acid (2-oxo-4-pentadec-1-enyl-[1,3]dioxan-5-yl)-amide (1)

N-palmitoylsphingosine ($C_{16}$-ceramide, 1.61 g, 3 mmol) was dissolved in dry THF (100 ml) with heating. The clear solution was brought to room temperature and N,N'-disuccinimidyl carbonate (1.92 g, 7.5 mmol) was added. Dimethylaminopyridine (DMAP 0.81 g, 7.5 mmol) was added with stirring and the reaction further stirred for 16 hours. The solvent was removed under reduced pressure and the residue was re-crystallized from n-heptane yielding 1.3 g (68%) of disuccinimidylceramidyl carbonate as white powder m.p. 73-76° C.

The stable product was obtained and identified by NMR and MS.

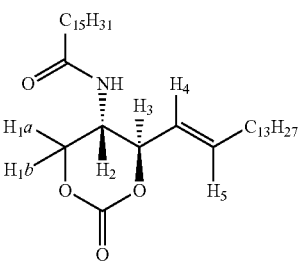

(1)

$^1$H NMR (CDCl$_3$) Sphingosine part, 4.21 (dd, 1H, 1a), 4.55 (d, 1H, 1b), 4.31 (d, 1H, 2), 8.06 (d, 1H, 2-NH), 4.95 (dd, 1H, 3), 5.49 (dd, 1H, 4), 5.81 (dt, 1H, 5), 2.04 (dt, 2H, 6), 1.35 (m, 2H, 7), 1.10-1.34 (m, 20H, 8-17), 0.82 (t, 3H, 18); Fatty Acid part, 2.22 (t, 2H, 2), 1.57 (quint, 2H, 3), 1.10-1.34 (m, 24 H, 4-15), 0.82 (t, 3H, 16); No free hydroxyl group is detected $^{13}$C NMR (CDCl$_3$) Sphingosine part, 68.28 (1), 44.71 (2), 82.20 (3), 124.01 (4), 137.20 (5), 32.42 (6), 29.22-29.73 (7-15), 32.07 (16), 22.88 (17), 14.10 (18), 148.45 (19, cyclic carbonate); Fatty Acid part, 174.04 (N—C=O), 36.14 (2), 25.71 (3), 29.35-29.91 (4-13), 31.88 (14), 22.65 (15), 14.08 (16);

MS: MH$^+$: 564

Example 2

Production of oxazoline (5-Pentadec-1-enyl-2-pentadecyl-4,5-dihydro-oxazol-4-yl)-methanol) (2)

A solution of the 15 g hexadecanoic acid (2-oxo-4-pentadec-1-enyl-[1,3]dioxan-5-yl)-amide (1), produced as described in Example 1, in hexane (250 ml) was refluxed for 2 hours and led to the conversion of the 6-membered ring to an oxazoline derivative as depicted below:

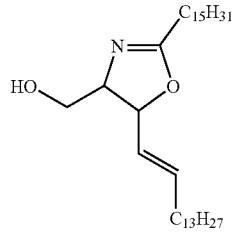

The product was identified by NMR.

$^1$H NMR (CDCl$_3$) Sphingosine part, 3.84 (dd, 1H, 1a), 3.93 (d, 1H, 1b), 3.55 (d, 1H, 2), 4.73 (dd, 1H, 3), 5.78 (dd, 1H, 4), 5.52 (dt, 1H, 5), 2.07 (dt, 2H, 6), 1.35 (m, 2H, 7), 1.10-1.34 (m, 20H, 8-17), 0.82 (t, 3H, 18); Fatty Acid part, 2.22 (t, 2H, 2), 1.57 (quint, 2H, 3), 1.10-1.34 (m, 24 H, 4-15), 0.90 (t, 3H, 16);

Example 3

Conjugation of Hexadecanoic acid (2-oxo-4-pentadec-1-enyl-[1,3]dioxan-5-yl)-amide (1) with amines

Example 3A

Conjugation of Hexadecanoic acid (2-oxo-4-pentadec-1-enyl-[1,3]dioxan-5-yl)-amide (1) with polyethyleneimine Hexadecanoic acid (2-oxo-4-pentadec-1-enyl-[1,3]dioxan-5-yl)-amide (1) (36 mg), 4-dimethylaminopyridine (DMAP, a hypernucleophilic acylation catalyst) (3 mg) and polyethylenimine, linear MW 2,500 (C$_2$H$_5$N)$_x$ (PEI, 160 mg) were dissolved in boiling chloroform (15 ml) and pyridine (15 ml) was added. Stirring of the mixture was continued for 90 minutes, after which the reactant, hexadecanoic acid (2-oxo-4-pentadec-1-enyl-[1,3]dioxan-5-yl)-amide, was not detected by TLC.

Two regioisomers were obtained as a result of the nucleophilic attack of the polyethyleneamine on the carbonate ring:

Example 3B

Conjugation of Hexadecanoic acid (2-oxo-4-pentadec-1-enyl-[1,3]dioxan-5-yl)-amide (1) with spermine Spermine (NH$_2$(CH$_2$)$_3$NH(CH$_2$)$_4$NH(CH$_2$)$_3$NH$_2$, 6.2 gr) was dissolved in pyridine (265 ml). To this solution was added dropwise a solution of hexadecanoic acid (2-oxo-4-pentadec-1-enyl-[1,3]dioxan-5-yl)-amide (1) (14.5 g) and DMAP (0.3 g) in dichloromethane (265 ml). The reaction mixture is allowed to stir at room temperature for 5 hours. The solvents were evaporated to dryness and the residue obtained was washed with acetonitrile (3×500 ml). The white solid residue was chromatographed over silica gel using a mixture of n-butanol, water, acetic acid (in a ratio of 6:2:2 respectively) as the eluting system to afford 20 g of pure products. Two amine-conjugated regioisomers were detected by NMR as a result of reacting hexadecanoic acid (2-oxo-4-pentadec-1-enyl-[1,3] dioxan-5-yl)-amide (1) with spermine:

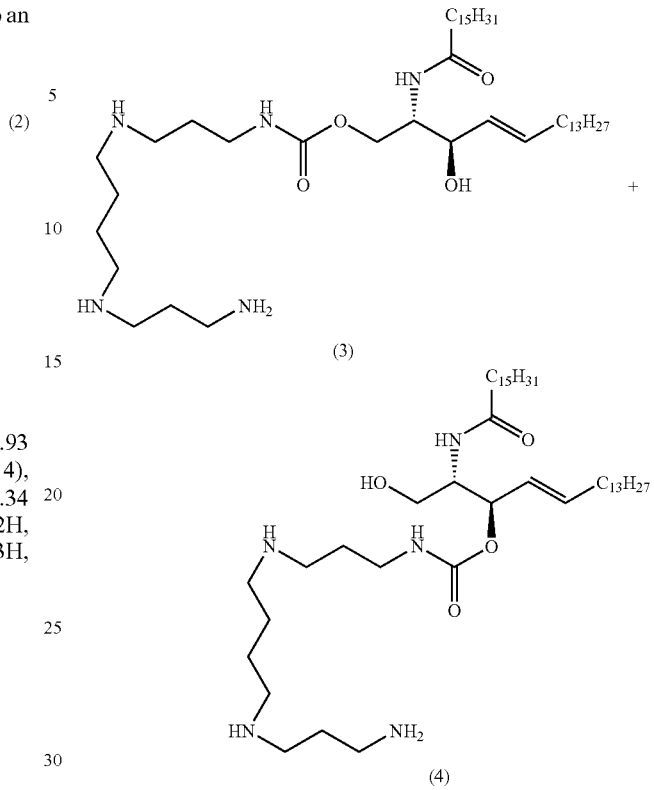

Under the reaction conditions of this specific example, the major isomer was determined as (3), and the minor isomer was (4). The ratio between isomer (4) and (3) is typically, but not exclusively, between 15 to 35% of isomer (4) vs. isomer (3). The above ratio can vary according operating conditions of the reaction, such as temperature, speed of addition, molar excess of spermine, dilution of the reaction medium, etc.

Example 4

Separation of amine-conjugated regioisomers 3 and 4 of Example 3B

The mixture of the two amine-conjugated regioisomers was separated by first treating it with the modifier, t-butoxycarbonyl (t-BOC) (protecting the amine moieties on the spermine residue) to obtain a mixture of two tri-BOC protected derivatives as illustrated below:

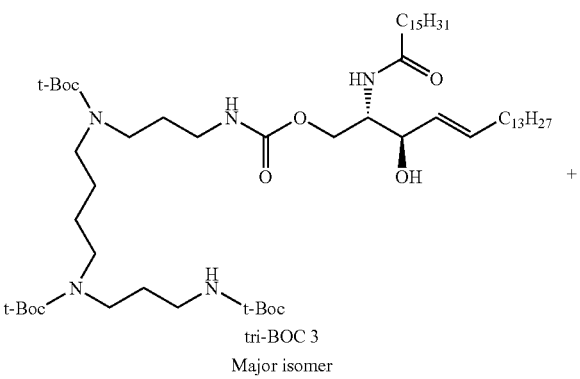

tri-BOC 3
Major isomer

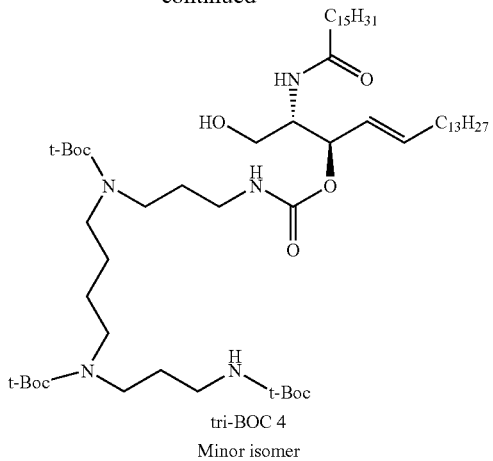

tri-BOC 4
Minor isomer

The two tri-BOC 3 and 4 were then separated by chromatography using a silica gel column and a mixture of ethyl acetate and hexane (in 50:50 ratio) as the eluting system.
TLC system: eluent: ethyl acetate:hexane (75:25 ratio respectively).
Rf: isomer 3: 0.75, isomer 4: 0.45.

After separation, deprotection of the t-Boc protecting groups may be performed using acidic conditions (HCl, or trifluoroacetic acid (TFA)).

In a typical procedure, tri-Boc 3 or tri-Boc 4 (450 mg) were dissolved in ethyl acetate (55 ml). To that solution was added concentrated hydrochloric acid HCl (2.5 ml). The solution was allowed to react overnight at room temperature. Solid sodium carbonate (2.5 g) was then added to neutralize the acidity of the medium. The solution was then evaporated to dryness and the compound extracted in a mixture of chloroform, water and methanol (32 ml:12 ml:16 ml ratio respectively). The chloroform phase was separated and evaporated to dryness to afford 300 mg of pure product The removal of the modifying groups is illustrated below:

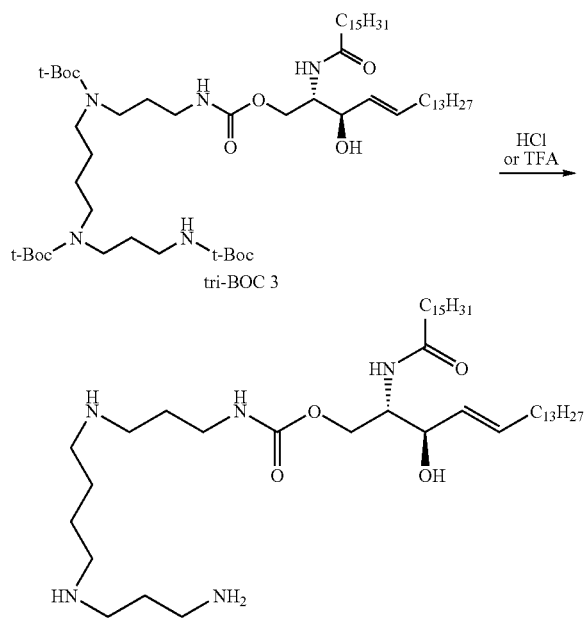

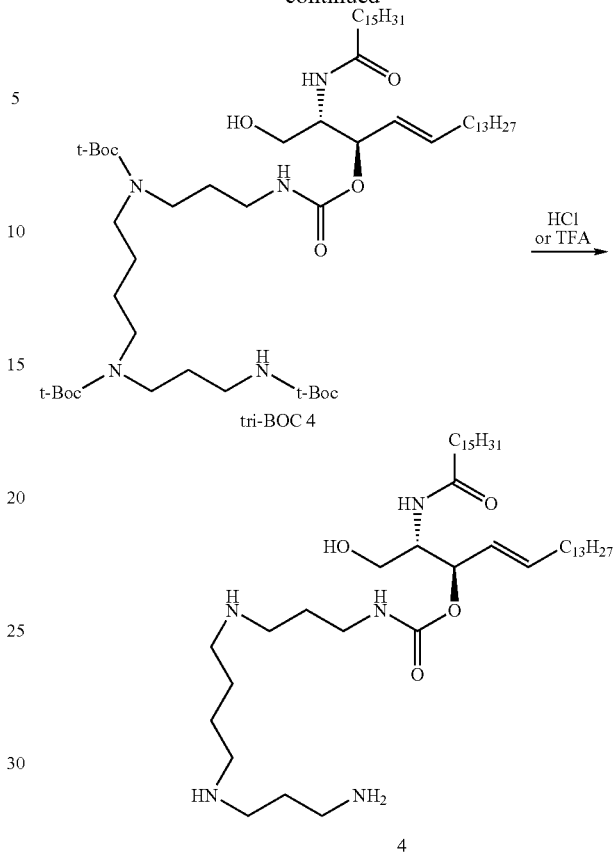

The separated products (compounds (3) and (4)) were identified by NMR and MS, as detailed below:

Compound (3)
$^1$H NMR (MeOH d4): Sphingosine part, 4.32 (1H), 4.05 (2H), 3.97 (1H) 5.44 (dd, 1H, 4), 5.71 (dt, 1H, 5), 2.03 (dt, 2H, 6), 1.35 (m, 2H, 7), 3.2 (2H), 2.95 (10H), 1.75 (4H) 1.86 (2H) 3.0 (10H) 1.10-1.34 (m, 20H, 8-17), 0.90 (t, 3H, 18); Fatty Acid part, 2.17 (t, 2H, 2), 1.57 (quint, 2H, 3), 1.10-1.34 (m, 24 H, 4-15), 0.90 (t, 3H, 16)
MS: 767 (MH+)

Compound (4)
$^1$H NMR (MeOH d4): Sphingosine part, 4.11 (dd, 1H), 5.07 (dd, 1H, 3), 5.39 (dd, 1H, 4), 5.78 (dt, 1H, 5), 3.6 (2H), 3.2 (2H) 2.95 (10H), 2.04 (dt, 2H, 6), 1.35 (m, 2H, 7), 1.10-1.34 (m, 20H, 8-17), 0.82 (t, 3H, 18); Fatty Acid part, 2.22 (t, 2H, 2), 1.57 (quint, 2H, 3), 1.10-1.34 (m, 24 H, 4-15), 0.82 (t, 3H, 16);
MS: 767 (MH$^+$)

Example 5

Conjugation of amine-conjugated regioisomer tri-BOC 4 of Example 3B with a second spermine Tri-BOC 4 (0.8 g) was dissolved in 30 ml of THF. DSC (290 mg) and DMAP (110 mg) were added at once to the previous solution. The reaction mixture was stirred overnight. The reaction mixture was transferred to a dropping funnel and was added dropwise to a solution of Spermine (761 mg) in 30 ml of pyridine during one hour at 0° C. The resulting reacting mixture was stirred overnight at room temperature. The solvents were evaporated to dryness and the resulting crude was chromatographed over siligel column chromatography using the eluting system of n-butanol-water-acetic acid (corresponding ratios of 5:1:1) to afford 1.1 g of compound (S).

The compound (S) (1.1 g) was suspended in ethyl acetate (100 ml) and HCl (5 ml) was added to the suspension. The reaction mixture was allowed to stir for one hour. The precipitate formed was filtered to afford 520 mg of material which is purified using silicagel chromatography with the eluting system of n-butanol-water-acetic acid (corresponding ratios of 3:1:1) to afford 336 g of pure compound (6).

The reaction of the amine-conjugated tri-BOC 4 as described in the present examples is illustrated in the following scheme:

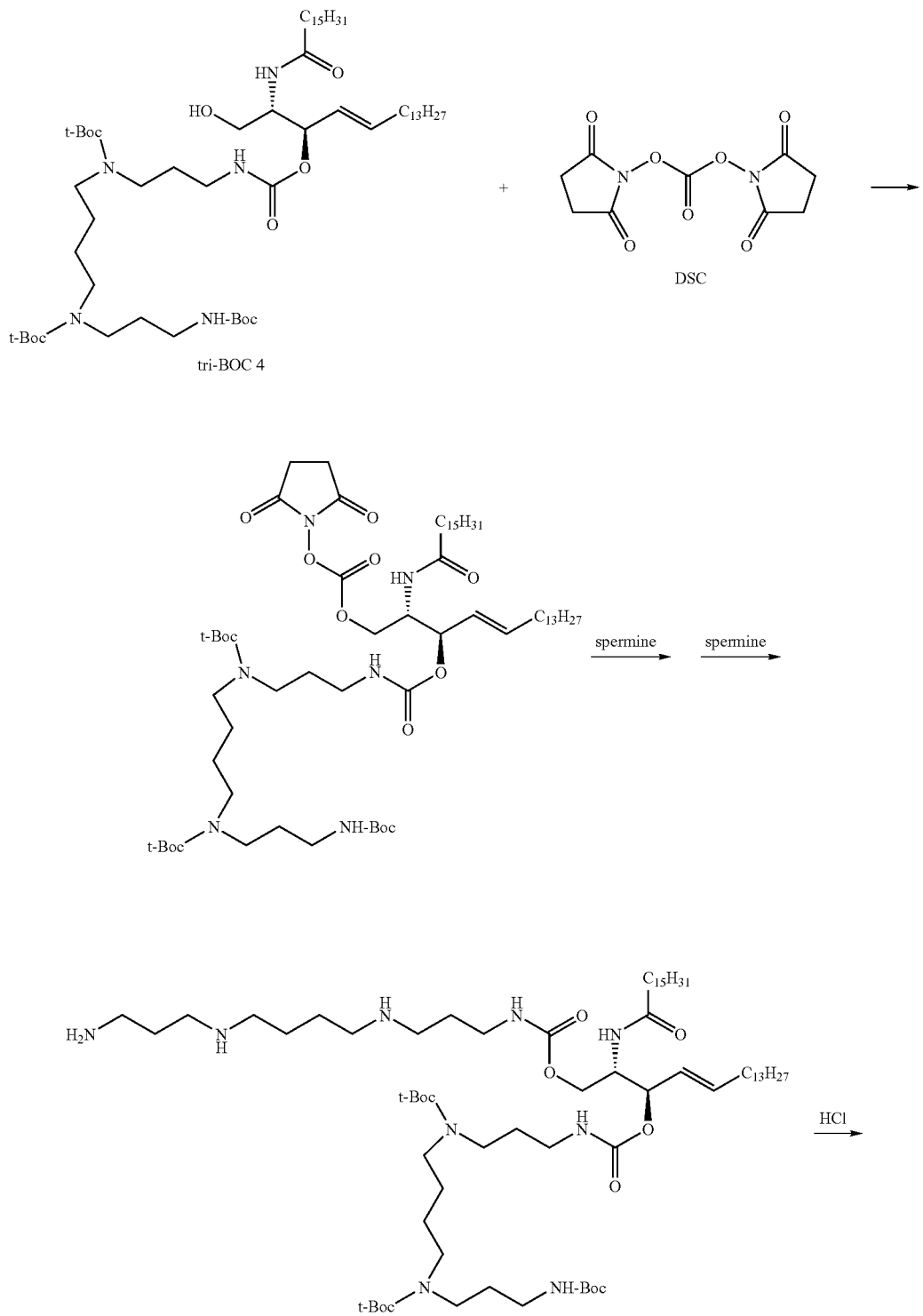

-continued

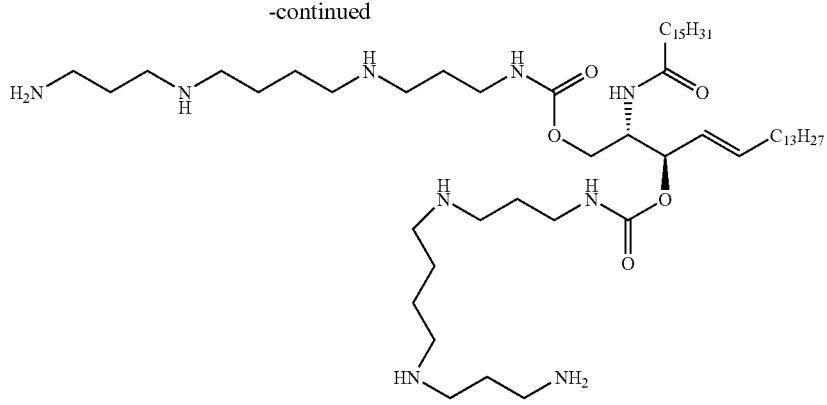

6

The invention claimed is:

1. A cyclic compound of general formula (I):

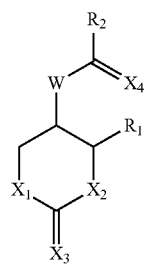

(1)

wherein
W represents O, S, NH, or $CH_2$;
$X_1$, $X_2$, $X_3$, and $X_4$ represent independently O or S; and
$R_1$ and $R_2$ independently represent a $C_1$-$C_{24}$ aliphatic moiety selected from the group consisting of alkyl, alkenyl and alkynyl, and at least one of $R_1$ and $R_2$ is an alkenyl chain.

2. The cyclic compound of claim 1, wherein $R_1$ and $R_2$ independently represent one of a branched and a linear $C_8$-$C_{24}$ chain.

3. The cyclic compound of claim 2, wherein $R_1$ and $R_2$ independently represent one of a branched and a linear $C_{12}$-$C_{18}$ chain.

4. The cyclic compound of claim 2, wherein $R_1$ is an alkenyl chain.

5. The cyclic compound of claim 1, wherein $R_1$ is an alkenyl chain and $R_2$ is an alkyl chain.

6. The cyclic compound of claim 1, wherein W represents NH.

7. The cyclic compound of claim 1, wherein $X_1$, $X_2$, $X_3$, and $X_4$ independently represent O.

8. The cyclic compound of claim 1, wherein $R_1$ is —CH=CH—$C_{13}H_{27}$ and $R_2$ is —$C_{15}H_{31}$.

9. The cyclic compound of claim 1, further comprising a first stereogenic carbon on position 4 and a second stereogenic carbon on position 5, each of the first and the second stereogenic carbon being independently in one of (R) and (S) configuration.

10. The cyclic compound of claim 1, wherein at least one of $R_1$ and $R_2$ is in one of (E) and (Z) configuration.

11. The cyclic compound (4R, 5S)-5-(hexadecanoylamido)-4-[(1E)-pentadecene]-[1,3]-dioxanone-2-one having formula (I):

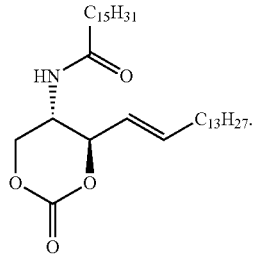

(1)

12. A process for preparation of a compound of general formula (I):

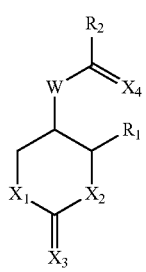

(1)

wherein
W represents O, S, NH, or $CH_2$;
$X_1$, $X_2$, $X_3$, and $X_4$ represent independently O or S; and
$R_1$ and $R_2$ independently represent a $C_1$-$C_{24}$ aliphatic moiety selected from the group consisting of alkyl, alkenyl and alkynyl, and at least one of $R_1$ and $R_2$ is an alkenyl chain;

the process comprising:

(a) providing a lipid of the following general formula (II):

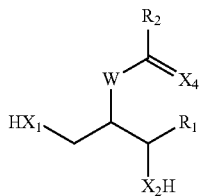
(II)

wherein
- W represents O, S, NH, or $CH_2$;
- $X_1$, $X_2$, $X_3$ and $X_4$ represent independently O or S; and
- $R_1$ and $R_2$ independently represent a $C_1$-$C_{24}$ aliphatic moiety selected from the group consisting of alkyl, alkenyl and alkynyl, and at least one of $R_1$ and $R_2$ is an alkenyl chain (b) allowing the lipid to react in a presence of a basic catalyst with a N,N'-disuccinimidyl derivative of general formula (III)

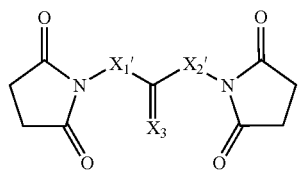
(III)

wherein $X_1'$, $X_2'$, and $X_3$ represent independently O or S; to obtain a substituted [1,3]-dioxan-2-one or a [1,3]-dioxan-2-thione (I).

13. The process of claim 12, wherein the lipid is an N-acyl sphingosine.

14. The process of claim 13, wherein the N-acyl sphingosine is selected from the group consisting of ceramide, dihydroceramide, phytoceramide, dihydrophytoceramide, ceramine, dihydroceramine, phytoceramine, dihydrophytoceramine and derivatives thereof.

15. The process of claim 14, wherein the ceramide is a $C_2$ to $C_{24}$ ceramide.

16. The process of claim 15, wherein the ceramide is a $C_8$ to $C_{24}$ ceramide.

* * * * *

UNITED STATES PATENT AND TRADEMARK OFFICE
CERTIFICATE OF CORRECTION

PATENT NO. : 8,541,605 B2
APPLICATION NO. : 12/599407
DATED : September 24, 2013
INVENTOR(S) : Aaron Garzon and Jean Hildesheim Page 1 of 1

It is certified that error appears in the above-identified patent and that said Letters Patent is hereby corrected as shown below:

Title Page, correct the spelling of the first Assignee's name as follows:

item (73) Assignees: Biolab Ltd.

In the Claims

Claim 12, Column 25, line 2, delete "the following".

(a)  providing a lipid of ~~the following~~ general formula (II):

Signed and Sealed this
Fourth Day of March, 2014

Michelle K. Lee
*Deputy Director of the United States Patent and Trademark Office*